(12) United States Patent
Wei

(10) Patent No.: US 11,419,985 B2
(45) Date of Patent: Aug. 23, 2022

(54) MEDICATION INJECTION DEVICE

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 865 days.

(21) Appl. No.: 16/077,042

(22) PCT Filed: Sep. 8, 2017

(86) PCT No.: PCT/US2017/050598
§ 371 (c)(1),
(2) Date: Aug. 9, 2018

(87) PCT Pub. No.: WO2018/049103
PCT Pub. Date: Mar. 15, 2018

(65) Prior Publication Data
US 2019/0046732 A1   Feb. 14, 2019

Related U.S. Application Data

(60) Provisional application No. 62/405,895, filed on Oct. 8, 2016, provisional application No. 62/393,168, filed on Sep. 12, 2016.

(51) Int. Cl.
*A61M 5/31* (2006.01)
*A61M 5/315* (2006.01)
(Continued)

(52) U.S. Cl.
CPC ........ *A61M 5/31513* (2013.01); *A61M 5/002* (2013.01); *A61M 5/2033* (2013.01);
(Continued)

(58) Field of Classification Search
CPC ........ A61M 5/24; A61M 5/28; A61M 5/2466; A61M 5/2459; A61M 2005/2474;
(Continued)

(56) References Cited

U.S. PATENT DOCUMENTS 1,393,720 A * 10/1921 Lomas .............. A61M 5/31595
12/142 N
1,718,605 A * 6/1929 Smith ..................... A61M 5/24
604/234

(Continued)

FOREIGN PATENT DOCUMENTS

FR    1320820 A * 3/1963 ............. A61M 5/24
GB    1193179 A * 5/1970 .......... A61M 5/2033

*Primary Examiner* — William R Carpenter
(74) *Attorney, Agent, or Firm* — Min Wei

(57) ABSTRACT

An injection device is provided herein comprising a container body for holding medication content having a distal end and a proximal end, the container body providing an outward flange at the distal end and a ledge at the proximal end; a piston placed at the proximal end of the container body for sealing and displacing medication content; a push rod placed inside the container body for moving the piston distally; and a connector providing an orifice for medication content delivery, placed at said distal end of said container body. The orifice in the connector provides medication content injection fluid pathway. With modification of the fundamental structure, a number of innovative device designs are created.

15 Claims, 15 Drawing Sheets

(51) Int. Cl.
*A61M 5/24* (2006.01)
*A61M 5/20* (2006.01)
*A61M 5/32* (2006.01)
*A61M 5/00* (2006.01)
*B65B 3/00* (2006.01)
*A61M 5/36* (2006.01)

(52) U.S. Cl.
CPC ............ *A61M 5/24* (2013.01); *A61M 5/3158* (2013.01); *A61M 5/3202* (2013.01); *A61M 5/3271* (2013.01); *B65B 3/003* (2013.01); *A61M 5/31591* (2013.01); *A61M 5/36* (2013.01); *A61M 2005/3107* (2013.01); *A61M 2005/3114* (2013.01); *A61M 2207/00* (2013.01)

(58) Field of Classification Search
CPC ...... A61M 5/281; A61M 5/286; A61M 5/285; A61M 5/288
See application file for complete search history.

(56) References Cited

U.S. PATENT DOCUMENTS

| | | | | |
|---|---|---|---|---|
| 1,725,318 A * | 8/1929 | Thayer | A61M 1/63 | 417/437 |
| 2,704,072 A * | 3/1955 | Sarnoff | A61M 5/283 | 604/138 |
| 2,844,148 A * | 7/1958 | Raife | A61M 5/31595 | 604/208 |
| 3,811,441 A * | 5/1974 | Sarnoff | A61M 5/2466 | 604/234 |
| 3,834,387 A * | 9/1974 | Brown | A61M 5/31513 | 604/125 |
| 4,129,130 A * | 12/1978 | Bigarella | A61M 5/28 | 604/243 |
| 4,226,236 A * | 10/1980 | Genese | A61M 5/284 | 604/125 |
| 5,318,544 A * | 6/1994 | Drypen | A61M 5/3155 | 604/211 |
| D387,874 S * | 12/1997 | Vila | D24/227 | |
| 5,782,815 A * | 7/1998 | Yanai | A61M 5/28 | 604/218 |
| 5,833,669 A * | 11/1998 | Wyrick | A61M 5/31595 | 604/234 |
| 8,777,906 B1 * | 7/2014 | Gray | A61M 5/315 | 604/189 |
| 9,737,667 B2 * | 8/2017 | Holmqvist | A61M 5/31595 | |
| 11,103,644 B2 * | 8/2021 | Bryant | A61M 5/31505 | |
| 2007/0250017 A1 * | 10/2007 | Carred | A61M 5/31501 | 604/220 |
| 2010/0292656 A1 * | 11/2010 | Groskopf | A61M 5/2466 | 604/200 |
| 2017/0290987 A1 * | 10/2017 | Mandaroux | A61M 5/3137 | |

\* cited by examiner

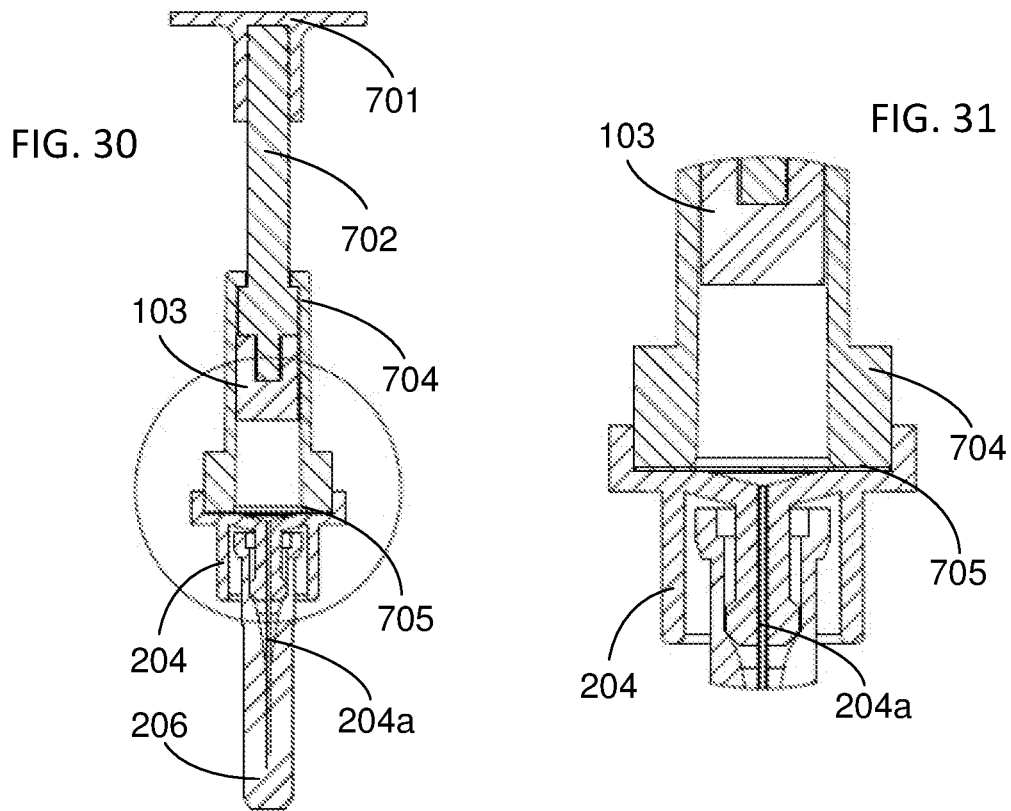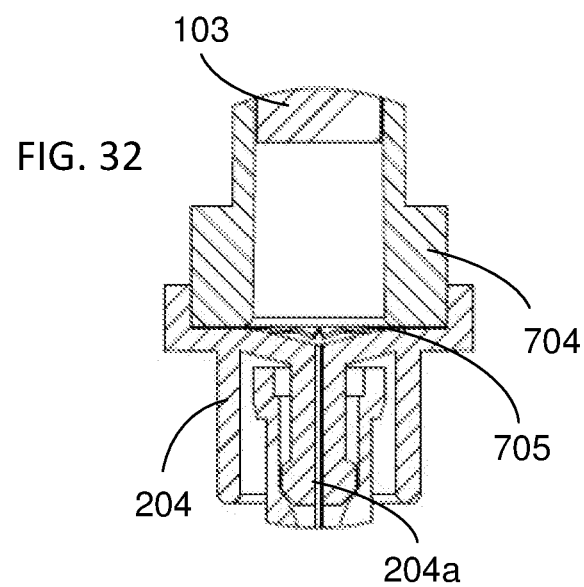

MEDICATION INJECTION DEVICE

TECHNICAL FIELD

The invention relates to a medication delivery device for delivering liquid medications.

BACKGROUND OF THE INVENTION

As injectable drugs increase in popularity, parenteral delivery devices are expected to be widely used. Injection drug delivery devices, such like the pre-filled syringe and autoinjectior devices, can ease medication preparation/administration and reduce needle injury, which results in improved patient convenience and compliance. Due to the advantages mentioned above, more patients and healthcare professionals prefer these devices over traditional manual syringes. However, current prefilled syringe is originally designed for manually drawing liquid medication from ampule or vial, and then delivering the medication solution through injection. This design lead to following challenges for advanced injection devices to deliver liquid dosage form in pre-filled format— a. Medication solution filling and syringe piston (seal component) placement happen at the same end of the syringe, which cause the unnecessary air bubble after dose filling. The air bubble is troublesome in certain situations. For example, air bubble has adverse effect for drug administration by intravenous (IV) push, or air bubble reduces dose accuracy for small dose injection (for example, intravitreal injection).

b. When plastic/polymer syringe is built based on current pre-filled syringe configuration, the syringe inner diameter at the needle end is often slightly smaller than the syringe inner diameter at the piston end because of injection molding manufacturing limit. On the other hand, the driving spring used in autoinjector for pre-filled syringe has less mechanical force when it reaches to the needle end of the syringe. This design conflict forces the device designer to use unnecessary strong spring, which often cause the failure of the device component(s) during storage or injection operation.

c. When glass syringe is built based on current glass pre-filled syringe configuration for luer lock connection, the luer lock has a potential to rotate during assembling with a luer lock needle.

d. Current pre-filled syringe design does not have feature to provide multiple injections from a single medication container precisely.

e. When small gauge needle, for example, 32G needle, is required for injection, current staked needle format is not feasible due to the design and manufacturing limits.

f. There have been known compatibility problems between the container/device components and the medication inside. For example, steel needle can generate Fe ions that cause the oxidization of epinephrine stored in pre-filled container in the epinephrine autoinjector. Tungsten ion in pre-filled glass syringe can cause the aggregation of protein drug stored in the syringe. Zinc impurity in needle shield of pre-filled syringe can lead to gelation of protein formulation. Furthermore, some medication formulation that use aggressive solvents or extremes of pH may not be suitable for being filled in pre-filled syringe with staked needle.

Therefore, injection devices based on a new design principal are in need.

SUMMARY OF THE INVENTION

It is an object of the present invention to provide a medication delivery device. This invention presents a series of the designs for the medication delivery device comprising: 1) a syringe-like container body to hold medication content, having a flange at medication filling end and a ledge at the opposite end; 2) a piston driven by a push rod that pushes the medication content out of the container body during injection; 3) a connector providing medication outflow pathway. This invention is to overcome one or more of the disadvantages of the prior art.

It is an advantage of the present invention that the medication filling into the device is from the medication injection end. Comparing to the medication filling from piston end, air bubble can be greatly reduced or even eliminated.

It is an advantage of the present invention that, in at least one embodiment, small dose, for example, 0.05 mL can be precisely delivered.

It is an advantage of the present invention that, in at least one embodiment, needle with small gauge, for example, 32G, can be incorporated with the device.

It is an advantage of the present invention that, in at least one embodiment, there is no luer lock rotation problem.

It is an advantage of the present invention that, in at least one embodiment, friction force between piston and container body gradually reduces during injection.

It is an advantage of the present invention that, in at least one embodiment, a new type of automatic medication delivery device with needle retraction mechanism is constructed.

It is an advantage of the present invention that, in at least one embodiment, air bubble can be precisely removed by user.

It is an advantage of the present invention that, in at least one embodiment, multiple doses can be precisely delivered.

It is an advantage of the present invention that, in at least one embodiment, incompatibility between medication content and needle as well as needle shield is eliminated.

It is an advantage of the present invention that, in at least one embodiment, no needle shield is needed for staked needle.

It is an advantage of the present invention that, in at least one embodiment, injection dose can be varied with using the same container body.

It is a further advantage of the present invention that, in at least one embodiment, different amount of formulation can be delivered based on medical need.

Due to the simplicity of operation and unique functional features, the medication delivery device embodiments of this invention are well suited for use by a wide range of healthcare professionals and patients including those with permanent or temporary disabilities.

BRIEF DESCRIPTION OF THE DRAWINGS

The figures are schematic and simplified for clarity, and they just show details, which are essential to the understanding of the invention, while other details are left out. Throughout, the same reference numerals are used for identical or corresponding parts.

FIG. 30 shows a cross-sectional view of the six alternative injection device assembly according to the invention.

FIGS. 31 and 32 show detailed cross-sectional views of the slit valve operation procedure of the six alternative injection device assembly according to the invention.

Corresponding parts are marked with the same reference symbols in all figures.

DETAILED DESCRIPTION THE DRAWINGS

Figure 1:
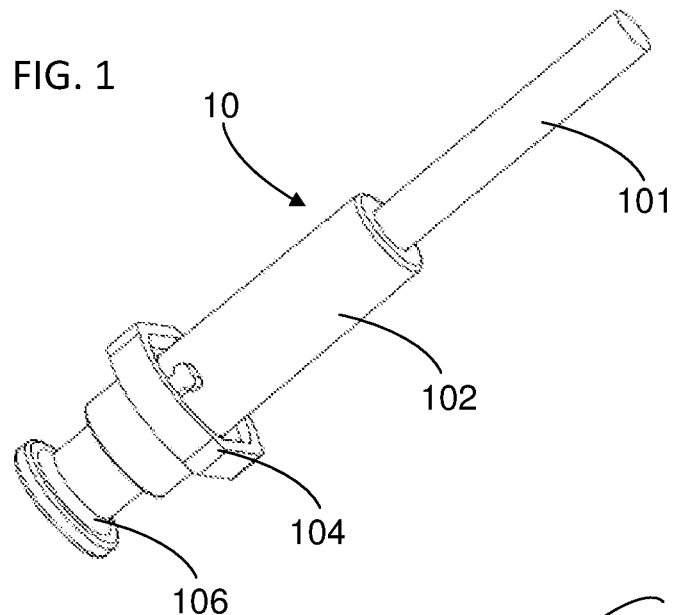
FIG. 1 shows a perspective view of an exemplary injection device assembly according to the invention.
Figure 2:
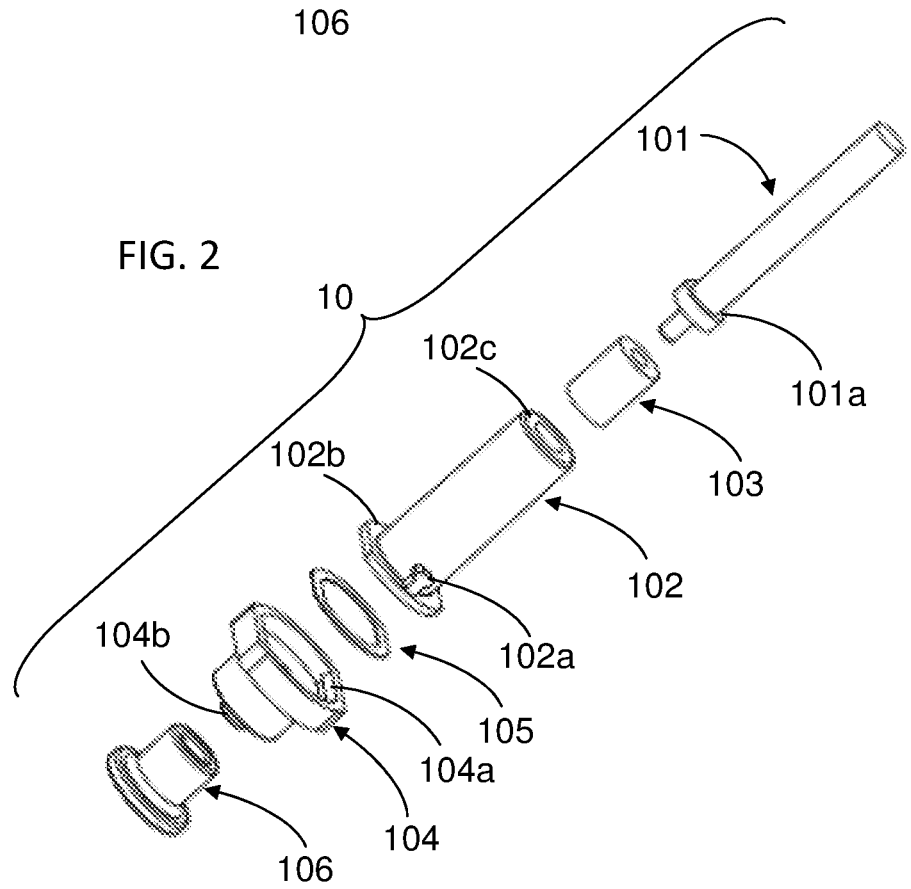
FIG. 2 shows an exploded view of the exemplary injection device assembly according to the invention.
Figure 3:
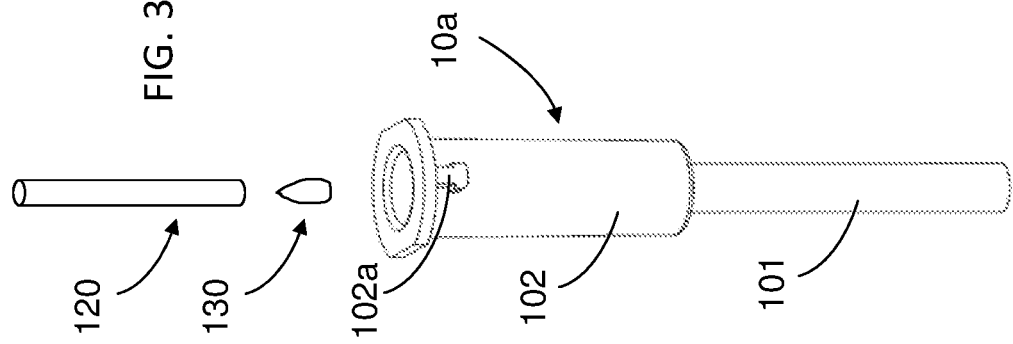
FIG. 3 shows medication filling process for the container body sub-assembly of the exemplary injection device assembly according to the invention.
Figure 4:
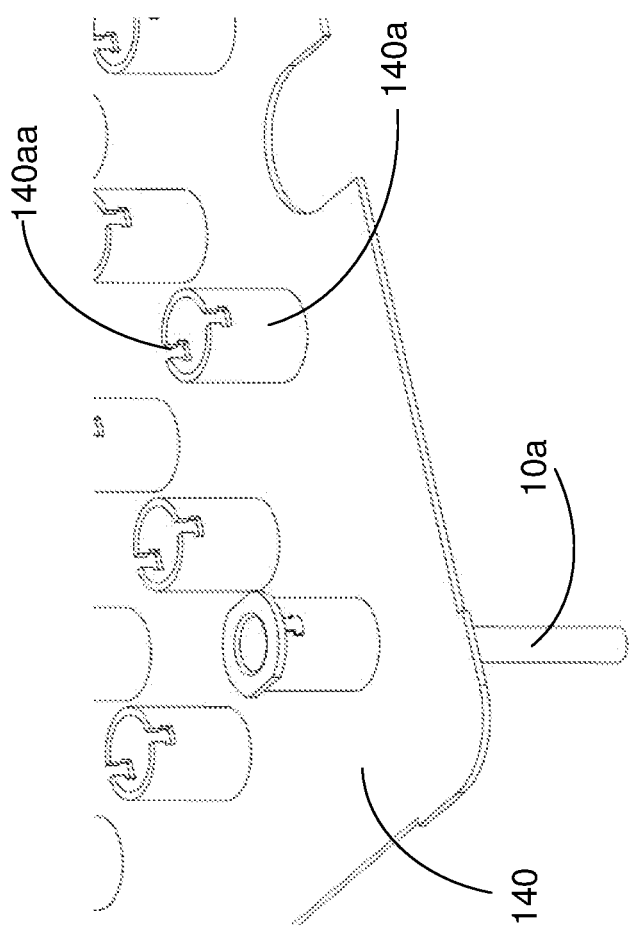
FIG. 4 shows the packaging configuration for the container body sub-assembly of the exemplary injection device assembly according to the invention.

The present invention will become more fully understood from the detailed description given hereinbelow and the accompanying drawings which are given by way of illustration only, and thus, are not limitive of the present invention, and wherein:

The apparatus and methods presented herein can be used for delivering any of a variety suitable therapeutic agents or substances, such as a drug, into a patient. Initially it may be convenient to define that, the term "distal end" is meant to refer to the end of the medication injection device assembly inserted into the patient, whereas the term "proximal end" is meant to refer to the end opposite to the "distal end" along the longitudinal axis of the device body. The words "upper", "lower", "right" and "left" designate directions in the drawings to which reference is made. The Words "inward" and "outward" refer to directions toward and away from, respectively, FIGS. 1-4 illustrate the construction and function mechanism of an exemplary injection device assembly 10 according to the invention. In this exemplary injection device assembly 10, a piston 103 is placed inside of a container body 102. Medication outflow pathway is through a connector 104 with luer lock feature 104b. The luer lock feature 104b has internal thread for luer lock connection. After tip cap 106 is removed, a luer lock needle can be attached to the injection device assembly 10 through the luer lock feature 104b. The container body 102 is assembled with the connector 104 though snap fit formed between an outward flange feature 102b on the container body 102 and snap feature 104a on the connector 104. This snap fit has orientation. Therefore, the luer lock rotation problem is avoided. There is an elastomer seal ring 105 is placed between the luer lock connector 104 and container body 102. The seal is optional when the luer lock connection 104 is assembled together with the container body 102 through welding or gluing process. A push rod 101 is placed at the proximal end of in the container body 102 and a shoulder design feature 101a is landed on an inward ledge feature 102c on the container body 102. During medication administration, the push rod 101 drives the piston 103 to move toward to the distal end of the container body 102. By this way, the medication is delivered. In this design, the inner diameter at distal end of the container body 102 can be larger than the inner diameter at proximal end of the container body 102. Therefore, the injection resistant force (friction force between piston and container body) can become less at later part of the injection process. In the drawings, FIG. 3 illustrates the medication formulation filling process for the injection device assembly 10. Here, medication filling happens at the distal end of the container body 102. During the medication filling, a sub-assembly 10a is placed in a cylindrical opening 140a of a nest 140 (a common format used in container filling process), through an engagement fit between feature 102a on the sub-assembly 10a and feature 140aa on the opening 140a. The engagement fit between feature 102a and feature 140aa also provides control of orientation of the sub-assembly 10a. The sub-assembly 10a is constructed by the push rod 101, the piston 103 and the container body 102. By this medication filling approach, air bubble size can be greatly reduced and even eliminated. After medication filling, seal ring 105, connector 104 and tip cap 106 are assembled together with the sub-assembly 10a for medication closure, though snap fit formed between the flange feature 102b on the container body 102 and feature 104a on the connector 104.

Figure 5:
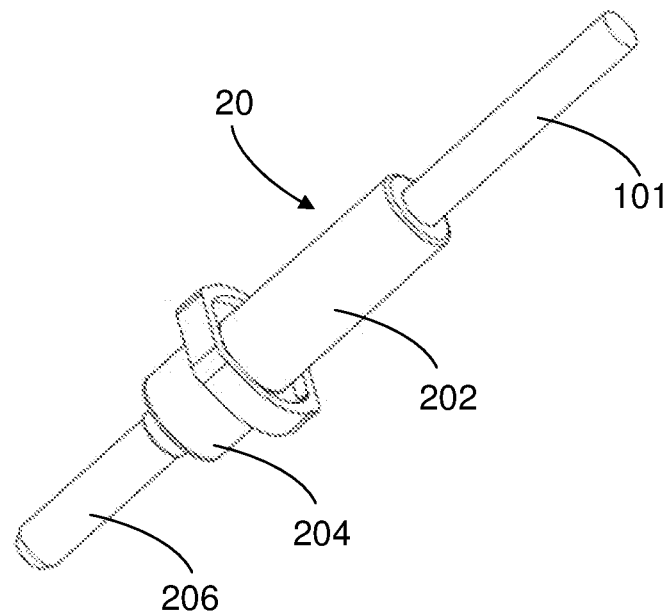
FIG. 5 shows a perspective view of the first alternative injection device assembly according to the invention.
Figure 6:
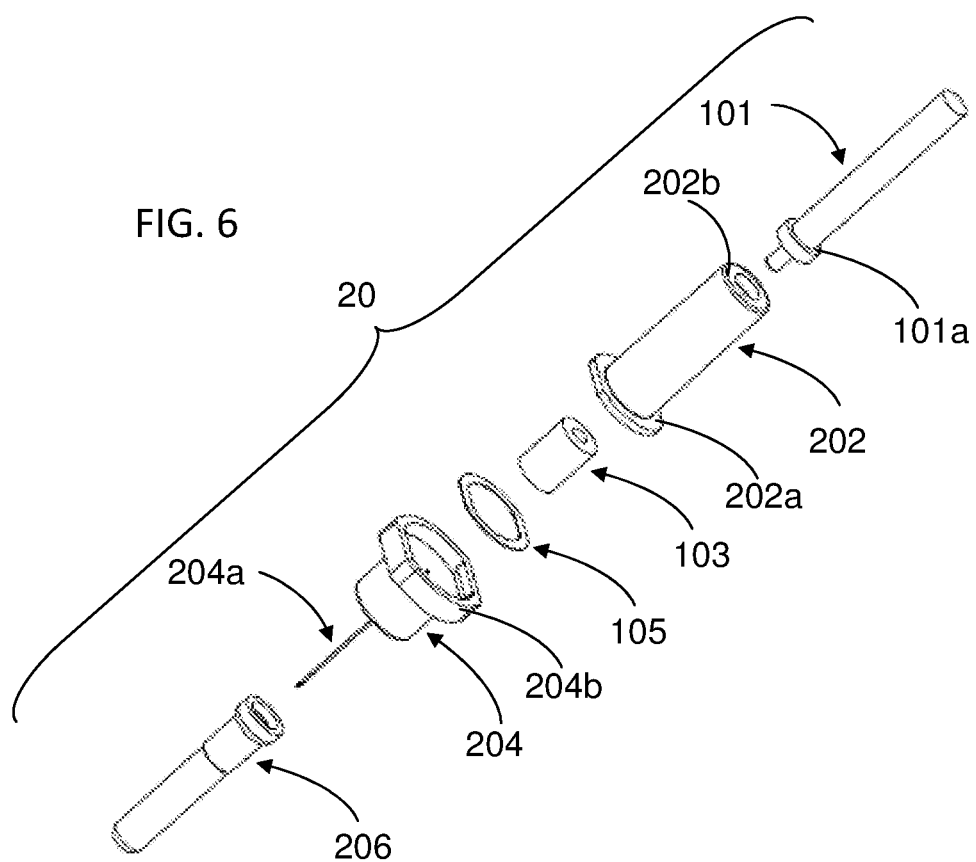
FIG. 6 shows an exploded view of the first alternative injection device assembly according to the invention.
Figure 7:
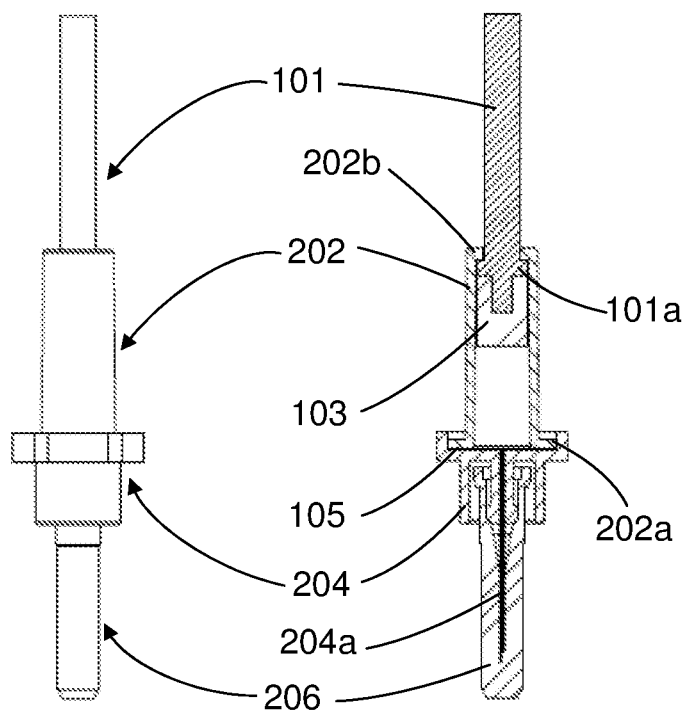
FIG. 7 shows a front view and a cross-sectional view of the first alternative injection device assembly according to the invention.

FIGS. 5-7 illustrate the construction and function mechanism of an exemplary injection device assembly 20 according to the invention. In this exemplary injection device assembly 20, the medication outflow pathway is through a hollow needle 204a. Here, the needle 204a is placed in a connector 204. An elastomer needle shield 206 is used to seal the opening on the hollow needle 204a. FIG. 7 illustrates the shoulder design feature 101a on push rod 101 is placed against an inward ledge feature 202b in a container body 202.

Figure 8:
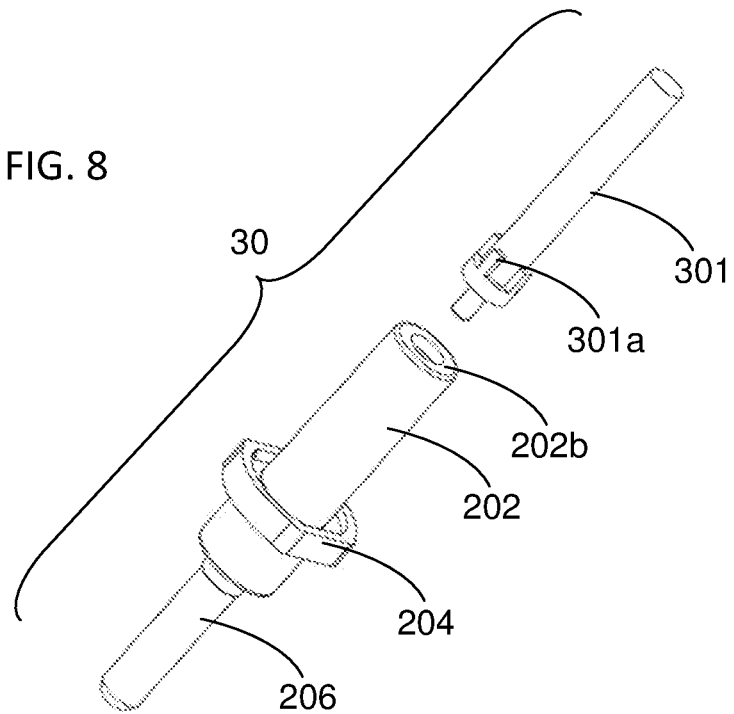
FIG. 8 shows an exploded view of the second alternative injection device assembly according to the invention.

FIG. 8 illustrates the construction and function mechanism of an exemplary injection device assembly 30 according to the invention. In this exemplary injection device assembly 30, a push rod 301 with spacer feature 301a is used. The spacer feature 301a is placed against the inward ledge feature 202b in the container body 202. By changing the length of the spacer feature 301a, piston 103 is placed at different position along the longitude axial of the container body 202. By this way, different filling volumes can be obtained with the same container body 202 without introducing air bubble.

Figure 9:
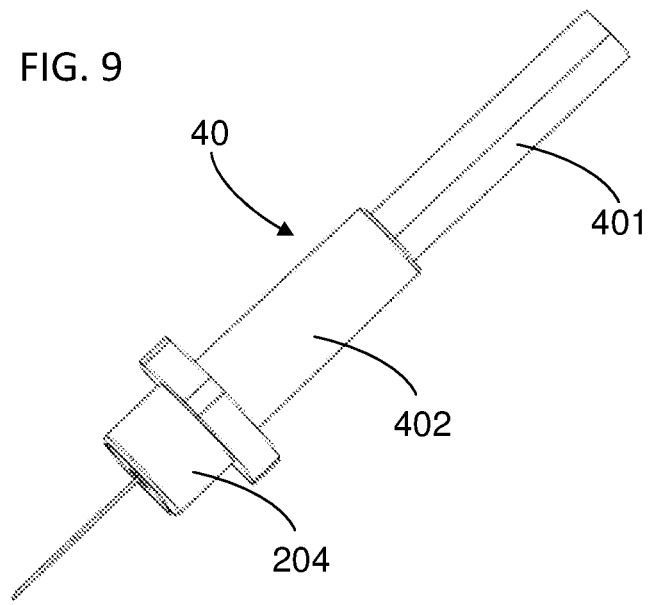
FIG. 9 shows a perspective view of the third alternative injection device assembly according to the invention.
Figure 10:
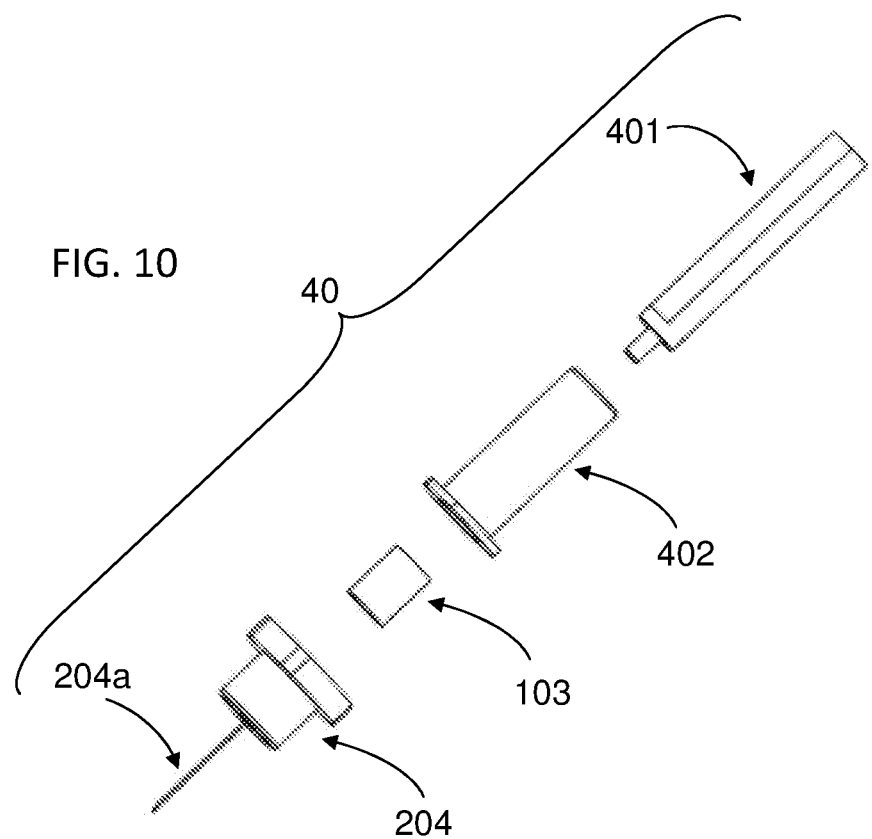
FIG. 10 shows an exploded view of the third alternative injection device assembly according to the invention.
Figure 11:
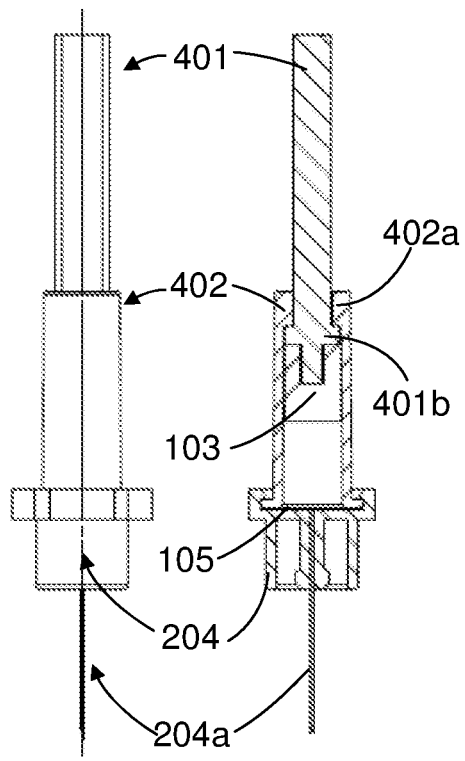
FIGS. 11 and 12 show a series of views of medication injection procedure of the third alternative injection device assembly according to the invention.
Figure 12:
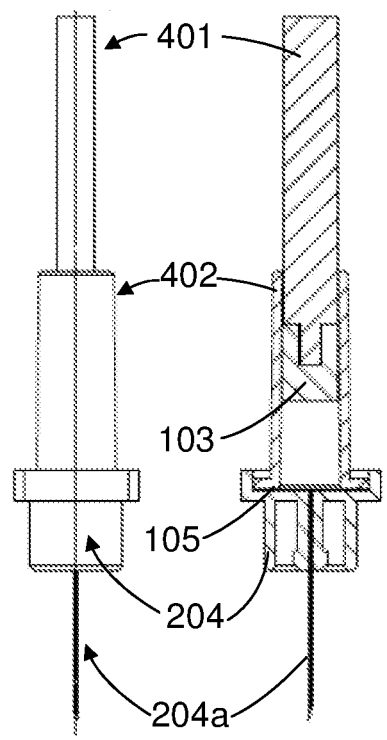
Figure 13:
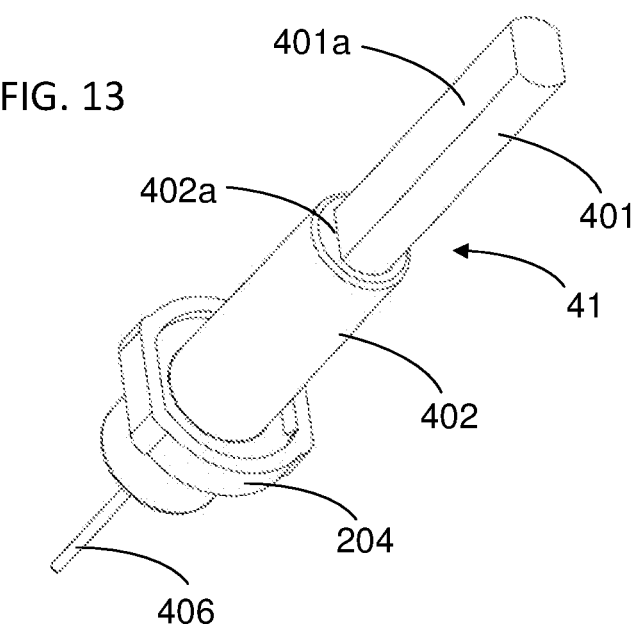
FIG. 13 shows a perspective view of another configuration of the third alternative injection device assembly according to the invention.
Figure 14:
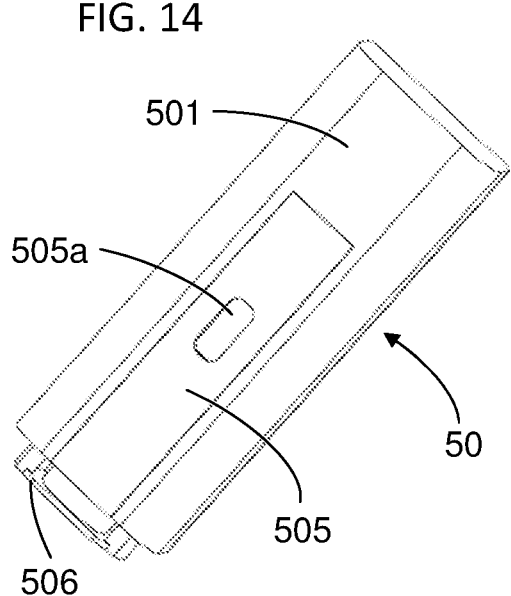
FIG. 14 shows a perspective view of the fourth alternative injection device assembly according to the invention.
Figure 15:
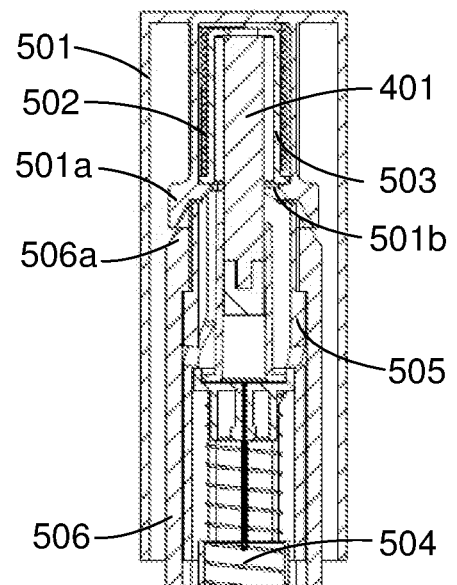
FIG. 15 shows a cross-sectional view of the fourth alternative injection device assembly according to the invention.
Figure 16:
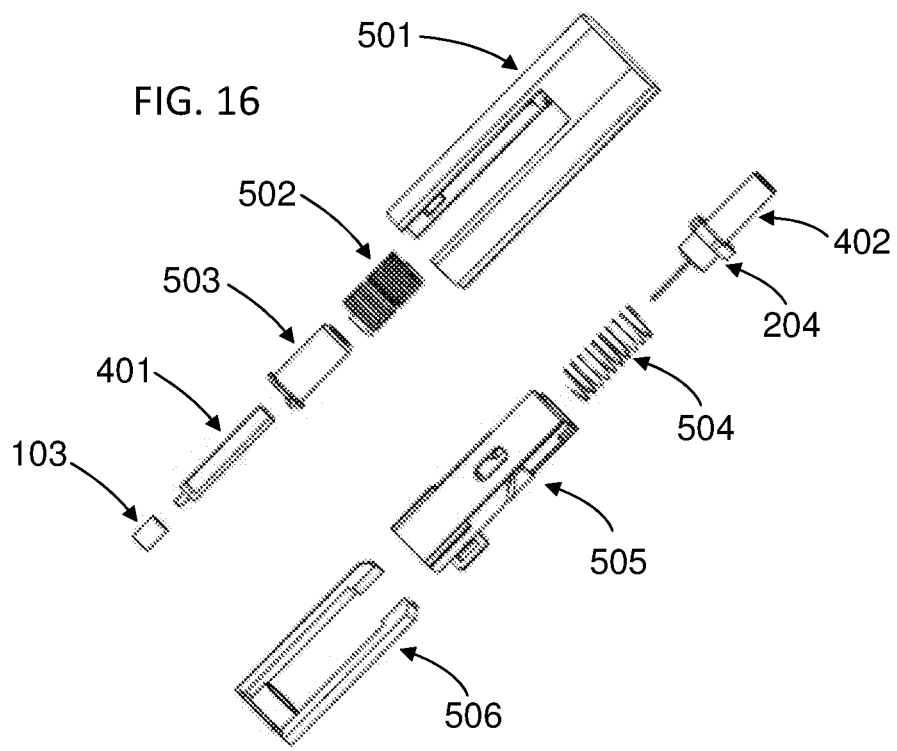
FIG. 16 shows an exploded view of the fourth alternative injection device assembly according to the invention.

FIGS. 9 and 10 illustrate the construction and function mechanism of an exemplary injection device assembly 40 according to the invention. In this exemplary injection device assembly 40, a push rod 401 with flat side feature 401a is used. The container body 402 is preferred to be made by plastic. For the container body 402, the inner diameter at the proximal end is preferred to be smaller than the inner diameter at the distal end. Because of the flat side feature 401a, the push rod 401 forms an aligned engagement with the container body 402, through oriented opening on a ledge feature 402a (shown in FIG. 11 and FIG. 13). FIGS. 11 and 12 show side views of the exemplary injection device assembly 40. In the side views, it can be seen that shoulder feature 401b is placed against the ledge feature 402a in the container body 402. FIG. 13 illustrates an alternative configuration of injection device assembly 40, injection device assembly 41. In the device assembly 41, a pierce-able needle shield 406 is used to protect needle 204a. During injection, the needle 204a can pierce through the needle shield 406 for medication injection.

Figure 17:
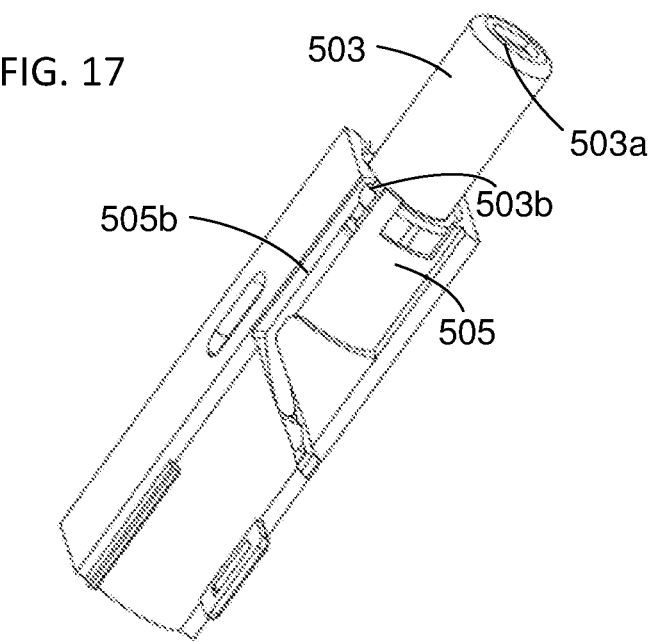
FIGS. 17, 18 and 19 show a series of the activation and medication injection procedure of the fourth alternative injection device assembly according to the invention.
Figure 18:
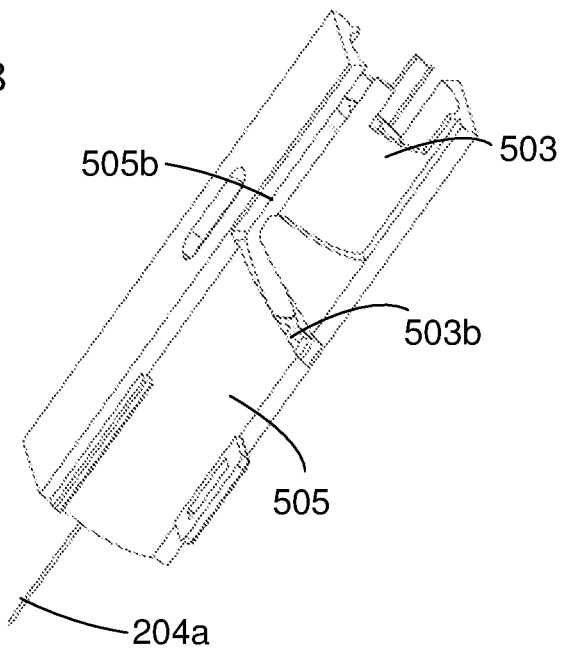
Figure 19:
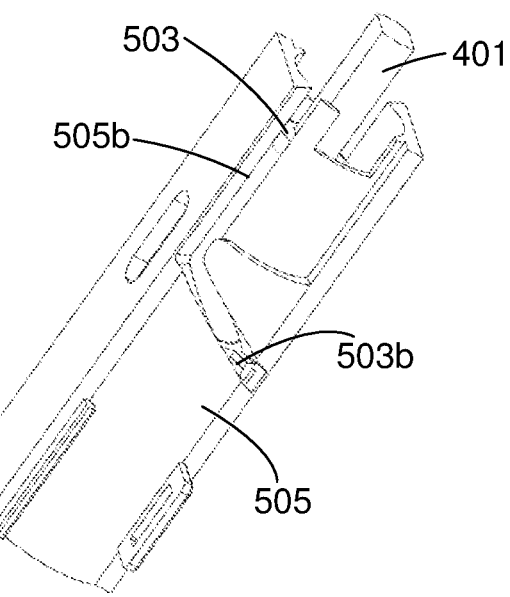

FIGS. 14 to 19 illustrate the construction and function mechanism of an exemplary injection device assembly 50 according to the invention. In this exemplary injection device assembly 50, the injection device assembly 41 is assembled with other components to form an autoinjector device. In the injection device assembly 50, a driving spring 502 is placed between an upper housing 501 and a push cap 503. The spring force generated from the driving spring 502 is applied on the push rod 401 through the push cap 503. There is an oriented window feature 503a and a key feature 503b on the push cap 503. When an activation bottom cap 506 is pushed against the injection site, the tapered feature 506a on the activation bottom cap 506 engages with the feature 501a on upper housing 501 and pushes the feature 501a to move outward. Consequently, the lock feature 501b on the upper housing 501 also moves outward and releases the push cap 503. The driving spring 502 then pushes the push cap 503 downward. The push cap 503 then pushes the push rod 401 downward. Because of the hydraulic resistance, the injection device assembly 41 is pushed downward and the needle 204a pierces through the needle shield 406 and is inserted into injection site for medication delivery. When the push cap 503 moves downward, the key feature 503b moves along track feature 505b on the housing 505. The track feature 505b has a straight portion and a sloped portion. At the end of the injection, the key feature 503b moves from the straight portion to the sloped portion in the track 505b and causes the push cap 503 to rotates (FIG. 17, 18). When the push cap 503 rotates to a position in that the push rod 401 is aligned with the oriented window feature 503a on the push cap 503, the push rod 401 is able to move upward by passing through the window feature 503a. Then, a bottom push spring 504 push the injection device assembly 41 move upward and the needle 204a is retracted from the injection site, after the medication is fully administrated (FIG. 19).

Figure 20:
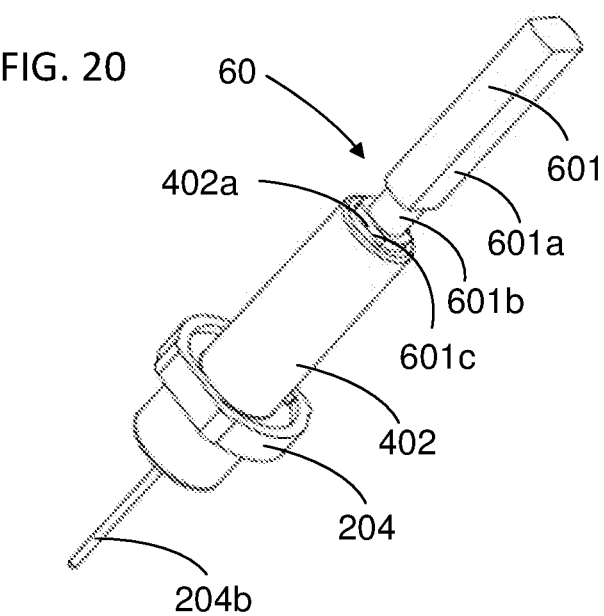
FIGS. 20 to 25 show a series of views of the activation and medication injection procedure of the fifth alternative injection device assembly according to the invention.
Figure 21:
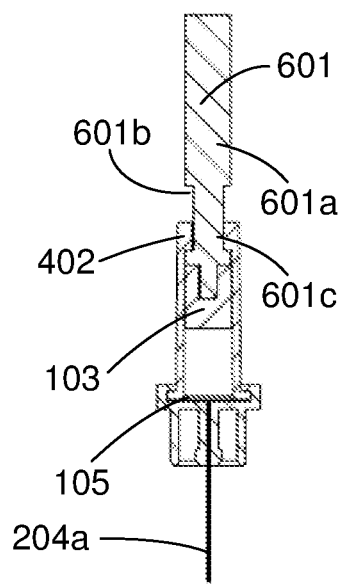
Figure 22:
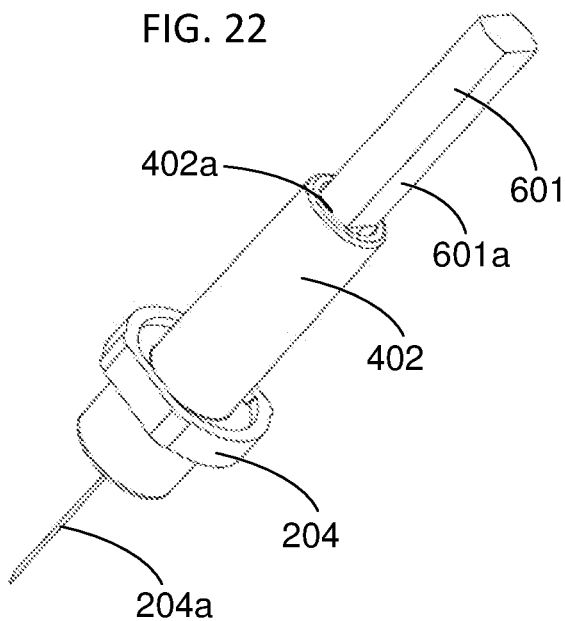
Figure 23:
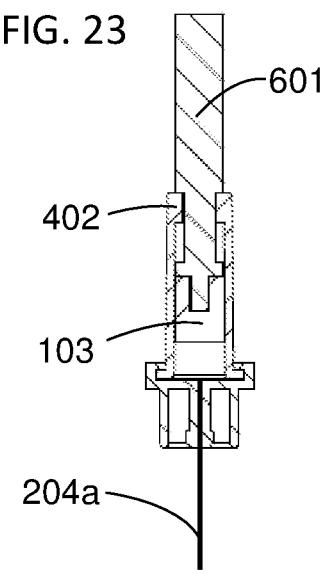
Figure 24:
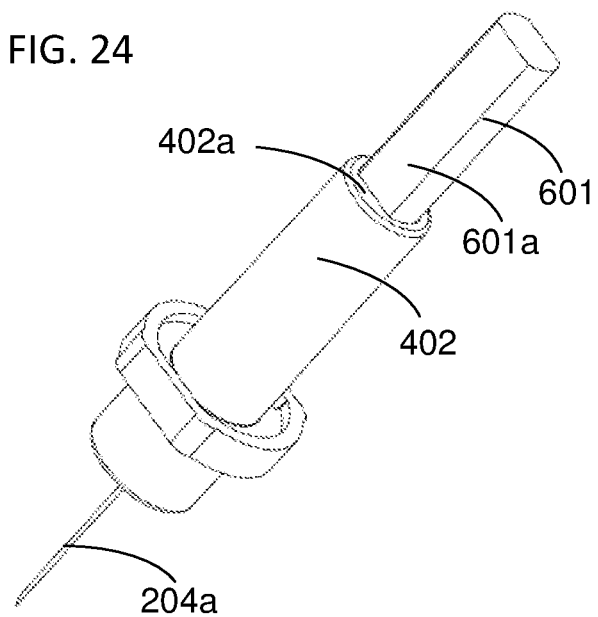
Figure 25:
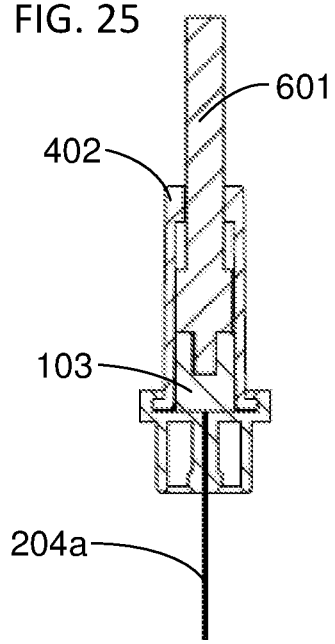
Figure 26:
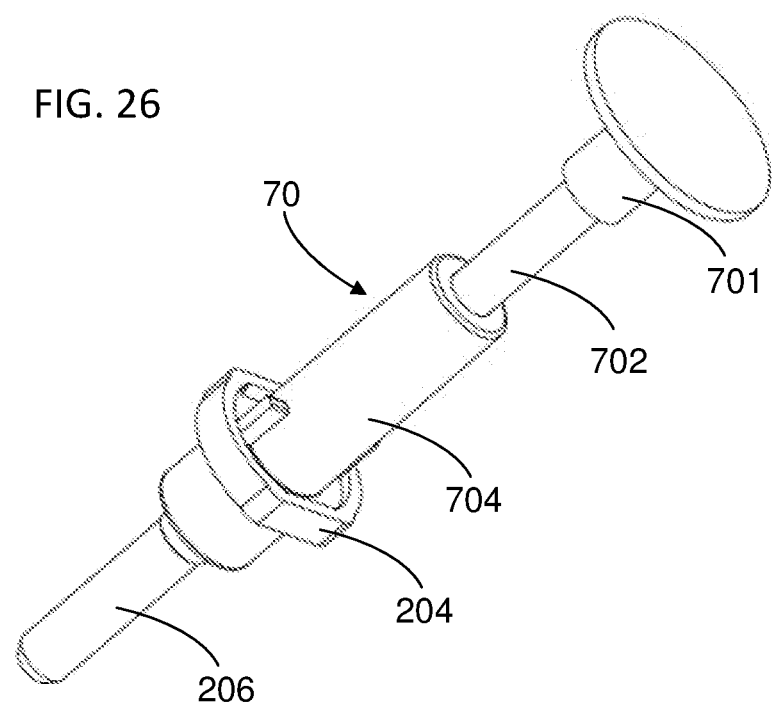
FIG. 26 shows a perspective view of the sixth alternative automatic medication delivery device assembly according to the invention.
Figure 27:
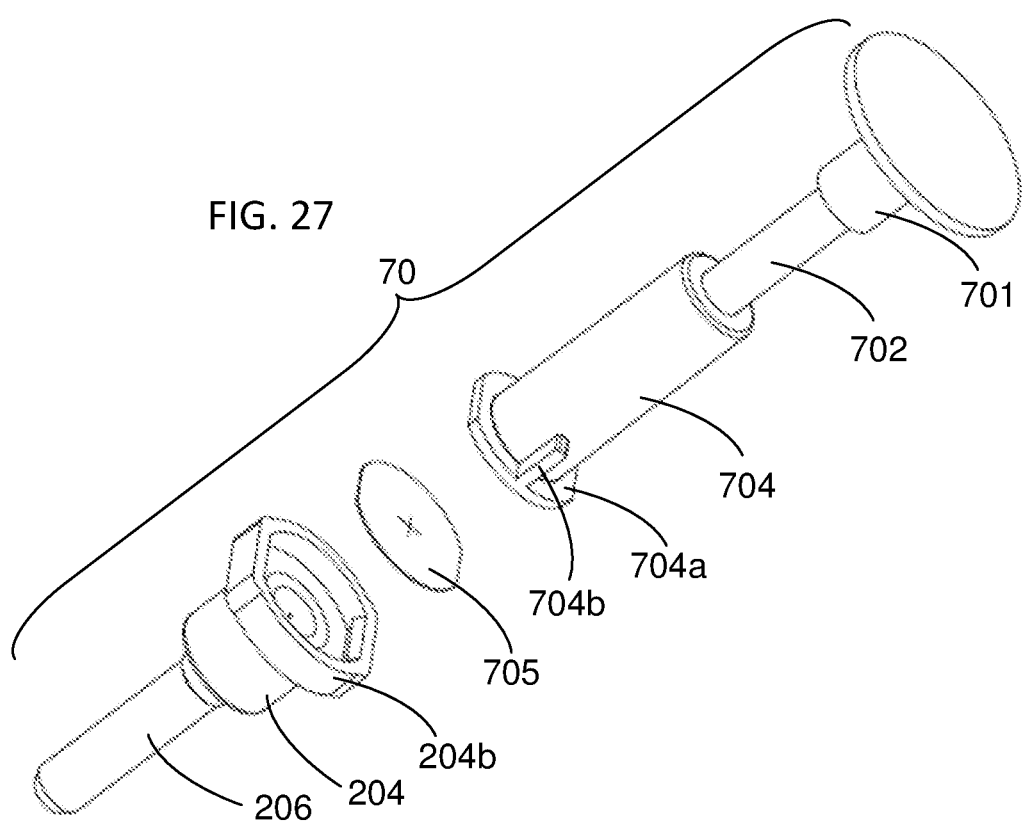
FIG. 27 shows an exploded view of the sixth alternative automatic medication delivery device assembly according to the invention.

FIGS. 20 to 25 illustrate the construction and function mechanism of an exemplary injection device assembly 60 according to the invention. In this exemplary injection device assembly 60, a push rod 601 is introduced. The push rod 601 has three sections, 601a, 601b and 601c. At the beginning of drug administration, 601c is aligned with the oriented opening on ledge feature 402a on the container body 402 (FIG. 20, 21). During drug administration, user pushes the push rod 601 toward to distal end and the push rod 601 stops when the section 601a is landed on the container body 402 (FIG. 22, 23). Because section 601b is a cylinder, user can rotate the push rod 601 90 degree so that the portion 601a is aligned with the oriented opening on ledge feature 402a on the container body 402. Then, user can further push the push rod 601 for the second dose (FIG. 24, 25). This embodiment introduce an approach to deliver multiple dosing using the invention here. This design is also advantageous for small dose injection, such as intravitreal injection. In intravitreal injection, air bubble need to be precisely removed before a small dose injection, for example, 0.05 mL. It is very difficult to precisely remove the air bubble without affecting the correct delivery dose if using traditional pre-filled syringe, because there is no physical stop. With the design of injection device assembly 60, user can first remove the air bubble by pushing the push rod 601 toward to distal end until it stops when the section 601a is landed on the container body 402. Then, user can rotate the push rod 601 so that the section 601a is aligned with the oriented opening on ledge feature 402a on the container body 402. Then, user can further push the push rod 601 for injecting small dose precisely.

Figure 28:
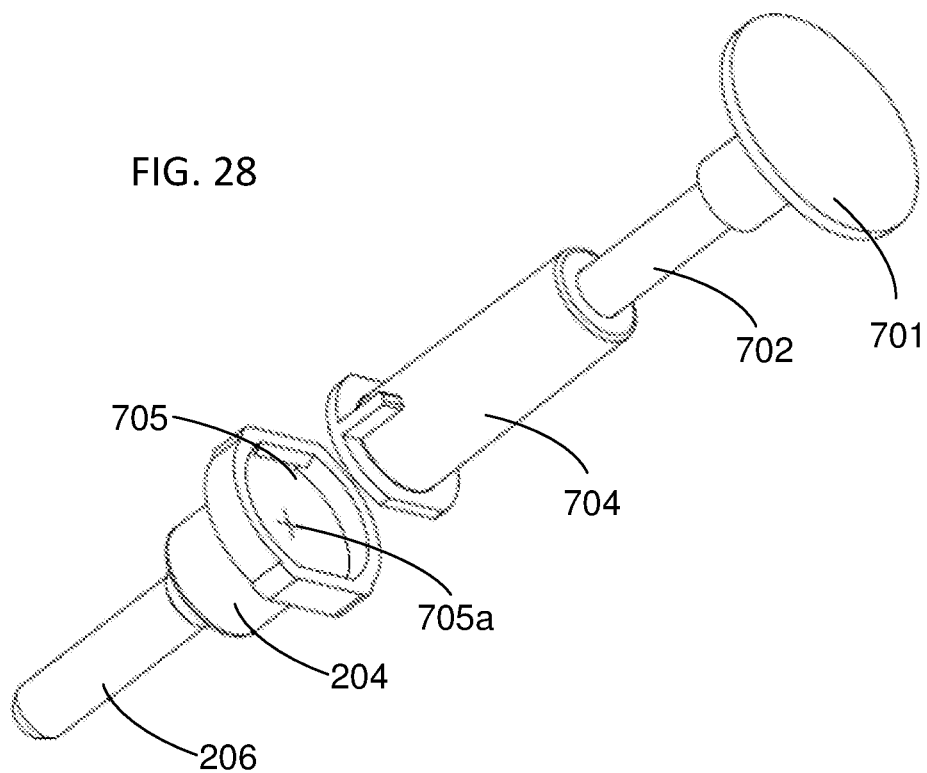
FIGS. 28 and 29 show a series of views of the slit valve operation procedure of the six alternative injection device assembly according to the invention.
Figure 29:
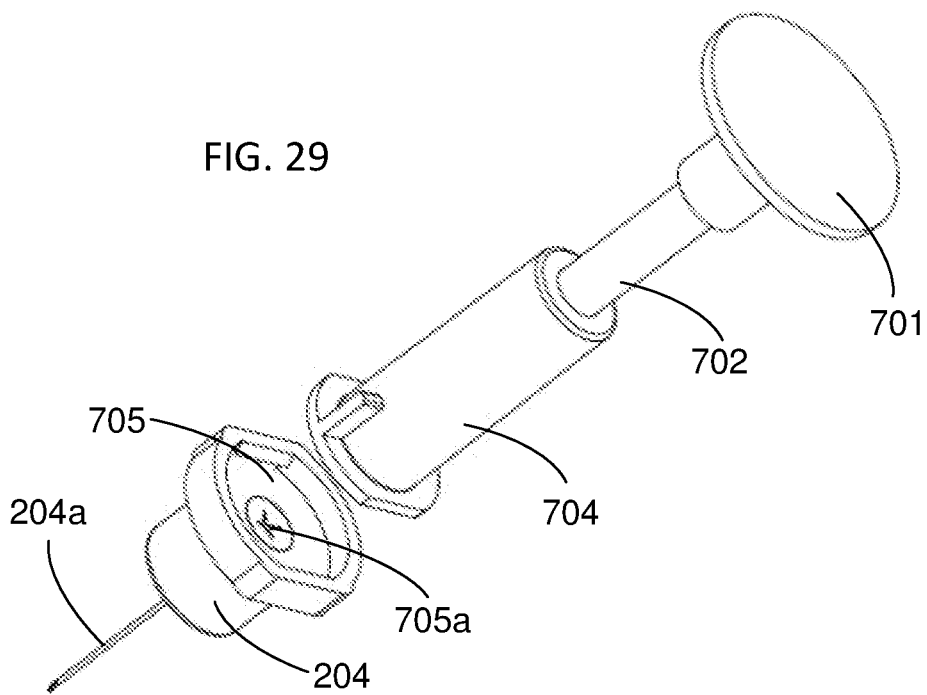

FIGS. 26 to 32 illustrate the construction and function mechanism of an exemplary injection device assembly 70 according to the invention. In this exemplary injection device assembly 70, a push rod 702 is placed at the proximal end of a container body 704. A piston 103 is assembled with the push rod 702. A finger push cap 701 is assembled with the push rod 702 at the proximal end. There is an elastomer sealable slit valve 705 is placed between the connector 204 and the container body 704. The elastomer sealable slit valve 705 serves as a barrier between filled medication in the container body 704 and the connector 204, as well as needle 204a and needle shield 206. The elastomer sealable slit valve 705 has a slit design feature 705a through its thickness, and is sufficiently resilient to prevent liquid flow through the slit under the weight of medication formulation inside the container body 704. With the elastomer sealable slit valve 705 in place, the medication formulation will not have contact with the needle connector 204, needle 204a and needle shield 206, before use. Therefore, any incompatibility issue between medication formulation and needle 204a as well as needle shield 206 is avoided. The connector 204 is assembled with the container body 704 through snap-fit between feature 204b and an outward flange feature 704a. Design feature 704b on the container body 704 is for controlling orientation of the container body 704 during medication filling. Before medication administration, user removes the needle shield 206 then insert the needle 204a into injection site. During medication administration, user applies force on the push cap 701. The push rod 702 drives the piston 103 to move toward to the distal end of the container body 704. During this process, the slit valve design feature 705a is opened by the hydraulic pressure of the medication formulation inside the container body 704, shown in FIGS. 29 and 32. Schematically, FIGS. 28 and 29 illustrate the elastomer sealable slit valve 705 in the closed and open positions, respectively. With the slit valve design feature 705a opened, the medication can be delivered through the needle 204a for medication administration.

Figure 33:
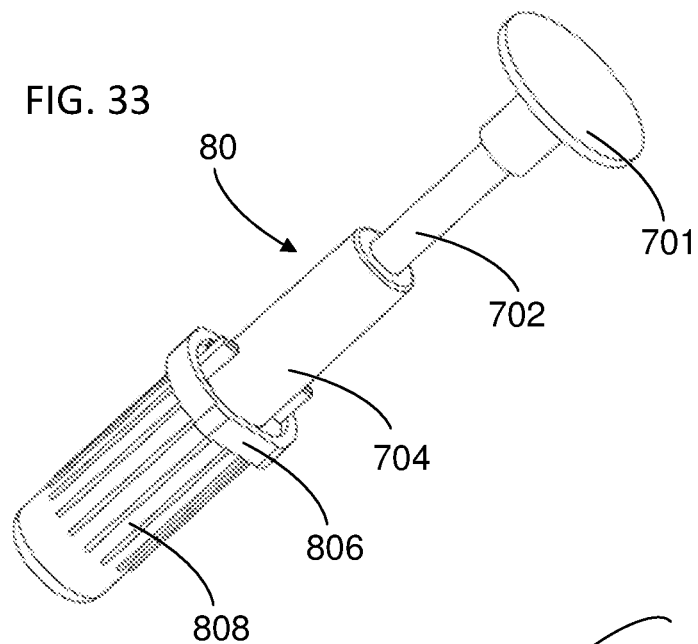
FIG. 33 shows a perspective view of the seventh injection device assembly according to the invention.
Figure 34:
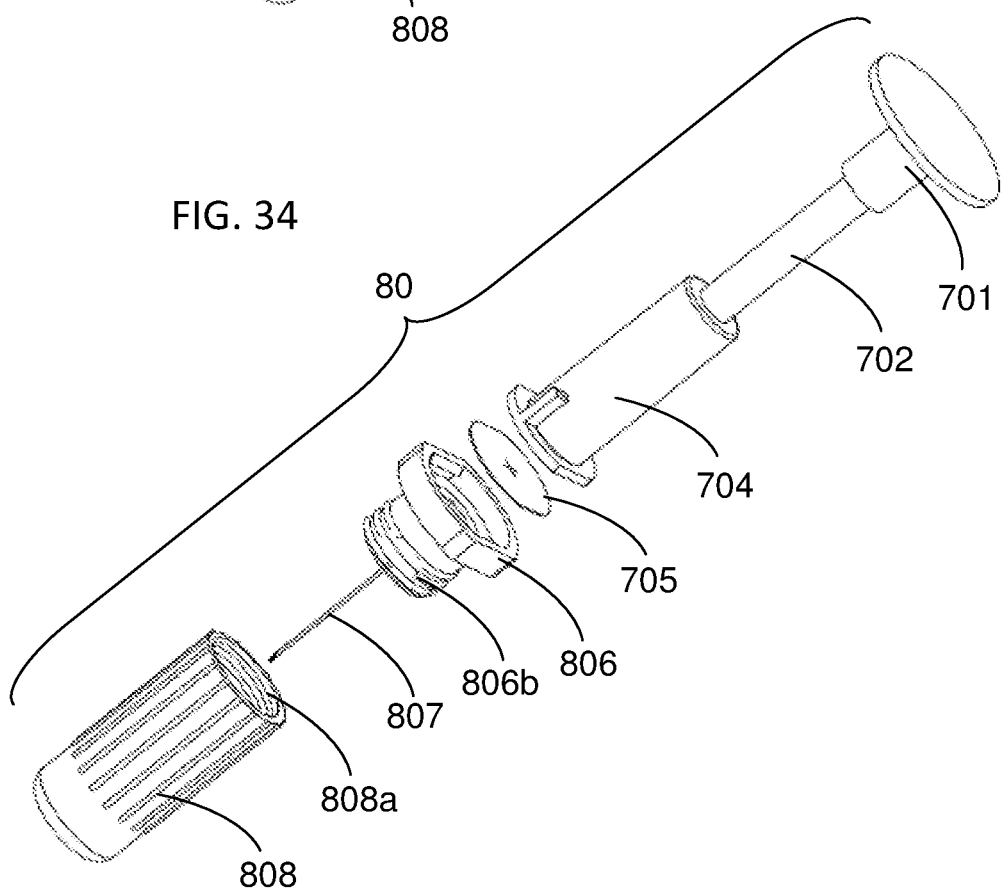
FIG. 34 shows an exploded view of the seventh injection device assembly according to the invention.

FIGS. 33 and 34 illustrate the construction and function mechanism of an exemplary injection device assembly 80 according to the invention. In this exemplary injection device assembly 80, a thread engagement between needle connector 806 and needle cap 808 provides sterile barrier for the device, through feature 806b on the needle connector 806 and feature 808a on the needle cap 808. Therefore, no needle shield is needed. This design provides advantage when small needle, for example, 32G, is used for injection, because this design avoid the problems of needle tip damage and needle bending when the needle is assembled with traditional elastomer needle shield. In this embodiment 80, the elastomer slit valve 705 also serves as a liquid seal between filled medication in the container body 704 and the needle connector 806.

Figure 35:
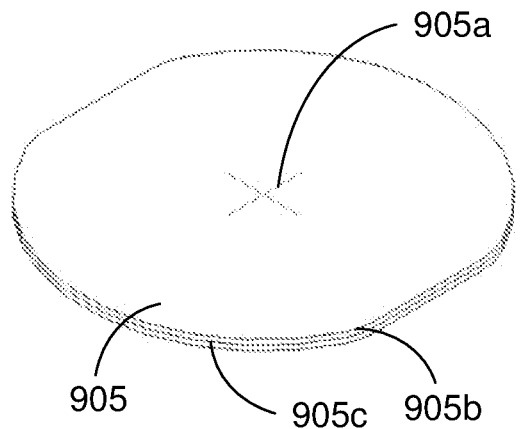
FIGS. 35 and 36 show alternative slit valve designs according to the invention.
Figure 36:
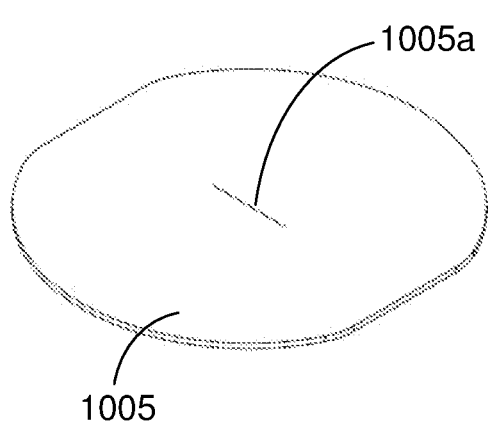

FIGS. 35 and 36 illustrate construction of two alternative designs to the elastomer component 705. In FIG. 35, elastomer sealable slit valve 905 has two layers. The formulation contact layer 905b can be more inert, more formulation compatible materials, such as Teflon or ethylene tetrafluoroethylene polymer. Also, the material for formulation contact layer 905b can be hydrophobic to reduce medication leakage through the slit valve during storage. The another layer 905c can be more elastic materials, such as silicone or rubber or thermoplastic elastomer (TPE) in order to provide seal function. The slit valve design feature 905a cuts through both layers. In FIG. 36, elastomer sealable slit valve 1005 has a different slit valve design 1005a. Different shapes of slit designs can be use for preventing leakage of different medication formulations. For example, low viscosity formulation uses a tighter slit.

Figure 37:
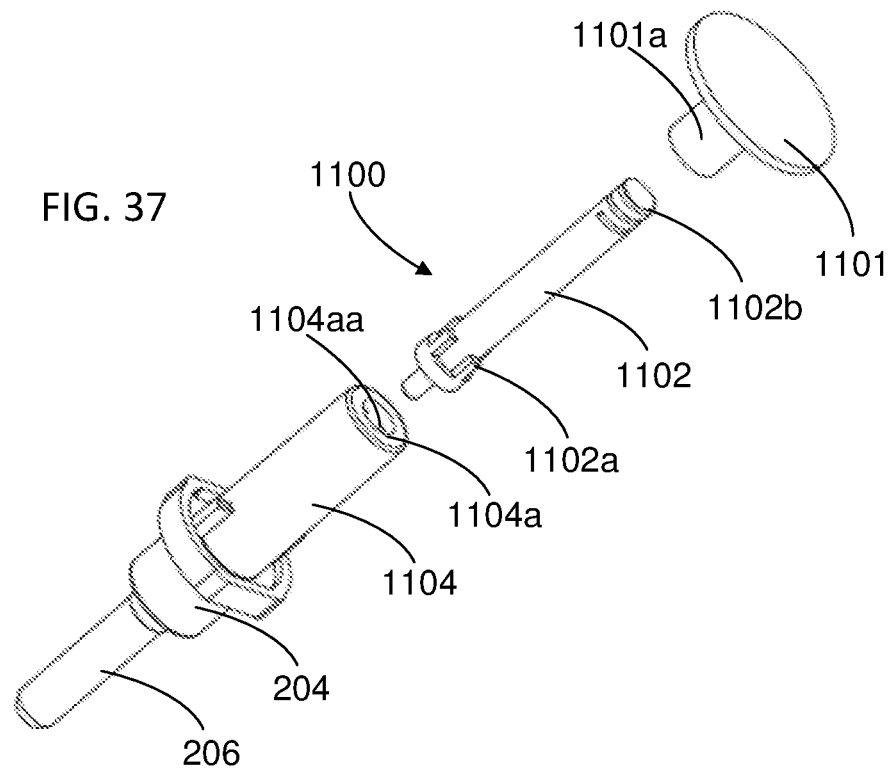
FIG. 37 shows a perspective view of the eighth alternative injection device assembly according to the invention.

FIG. 37 illustrates the construction and function mechanism of an exemplary injection device assembly 1100 according to the invention. In the embodiment 1100, the container body 1104 has a groove feature 1104aa on a ledge feature 1104a, and a push rod 1102 has a rib feature 1102a. When the container body 1104 is assembled with the push rod 1102, the rib feature 1102a is interlocked with the groove feature 1104aa. As the result, the push rod 1102 will not rotate against the container body 1104. Then, push cap 1101 is assembled with the push rod 1102 through a thread engagement between feature 1102b and feature 1101a. The medication delivery stops when feature 1101a lands on the container body 1104. Therefore, the length of 1101a can be varied in order to achieve different amount of medication delivered based on medical need.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An injection device comprising:
a container body for holding medication content having a distal end and a proximal end, and an outward flange at said distal end of said container body and an inward ledge with an oriented opening at said proximal end of said container body;
a piston placed at said proximal end of said container body for sealing and displacing medication content;
a push rod placed inside said container body for moving said piston distally, wherein said push rod has a distal end and a shoulder feature at said distal end of said push rod, and wherein during assembly said push rod and said shoulder feature are configured to be inserted into said container body from said distal end of the container body;
wherein said push rod has a flat side feature cooperating with said oriented opening at said inward ledge to define multiple sections on said push rod wherein said multiple sections allow the push rod to be rotated with respect to the oriented opening to define multiple piston displacements for dosing; and
a connector providing an orifice for medication content delivery, placed at said distal end of said container body.

2. The injection device as in claim 1 further comprising a seal ring placed between said container body and said connector.

3. The injection device as in claim 1 further comprising a luer lock configuration in said connector.

4. The injection device as in claim 1 further comprising a needle staked in said connector.

5. The injection device as in claim 4 further comprising a needle shield to protect said needle.

6. The injection device as in claim 4 further comprising a sealable valve, placed between said container body and said connector, for preventing medication content from contacting said needle before injection.

7. The injection device as in claim 6 further comprising a mechanical seal to maintain sterility for said needle.

8. The injection device as in claim 1 wherein inner diameter at said distal end of said container body is larger than inner diameter at said proximal end of said container body.

9. The injection device as in claim 1 wherein said push rod providing a spacer to control medication content filling volume.

10. The injection device as in claim 1 further comprising a push cap engaged with said push rod to control medication content injection volume.

11. The injection device as in claim 1 wherein said medication content is pre-filled into said container body.

12. The injection device as in claim 1 wherein said medication content is for intravitreal injection.

13. The injection device as in claim 12 wherein injection volume of said medication content is less than or equal to 0.05 mL.

14. A container body packaging assembly, comprising:
at least one injection device;
a panel including an upper surface;
a plurality of openings defined in said panel, wherein said panel and said plurality of openings are integrally formed as a unitary structure and each of said openings configured to removably receive a container body assembly of the at least one injection device, said container body assembly including:
a container body configured for holding medication content and having a distal end and a proximal end and an outward flange at said distal end of said container body and an inward ledge with an oriented opening at said proximal end of said container body, wherein said proximal end of said container body is sealed by a piston placed therein for sealing and displacing medication content and assembled with a push rod placed inside said container body for moving the piston distally, wherein said push rod has a distal end and a shoulder feature at said distal end of said push rod, wherein during assembly said push rod and said shoulder feature are configured to be inserted into said container body from said distal end of said container body, wherein said push rod has a flat side feature cooperating with said oriented opening at said inward ledge to define multiple sections on said push rod wherein said multiple sections allow the push rod to be rotated with respect to the oriented opening to define multiple piston displacements for fixed dosing; and a connector providing an orifice for medication content delivery, to be placed at said distal end of said container body;

and wherein said upper portion of said opening defines a holding means configured to support said container body assembly such that said distal end of said container body is stabilized in said opening.

15. A method of producing pre-filled injection device comprising the steps of:

Providing an injection device comprising a container body assembly including:

a container body for holding medication content and having a distal end and a proximal end and an outward flange at said distal end of said container body and an inward ledge with an oriented opening at said proximal end of said container body, a piston placed at said proximal end of said container body for sealing and displacing medication content, and a push rod placed inside said container body for moving said piston distally, wherein said push rod has a distal end and a shoulder feature at said distal end of said push rod, wherein during assembly said push rod and said shoulder feature are configured to be inserted into said container body from said distal end of said container body and wherein said push road has a flat side feature cooperating with said oriented opening at said inward ledge to define multiple sections on said push rod wherein said multiple sections allow the push rod to be rotated with respect to the oriented opening to define multiple piston displacements for fixed dosing; and Placing said container body assembly into a panel with a plurality of openings defined in said panel;

Filling medication content from said distal end of said container body assembly; and Placing a connector providing an orifice for medication content delivery at said distal end of said container body assembly.

* * * * *